United States Patent [19]

Hayakawa et al.

[11] 4,382,892
[45] May 10, 1983

[54] BENZOXAZINE DERIVATIVES

[75] Inventors: Isao Hayakawa; Tokiyuki Hiramitsu; Yoshiaki Tanaka, all of Tokyo, Japan

[73] Assignee: Daiichi Seiyaku Co., Ltd., Tokyo, Japan

[21] Appl. No.: 298,816

[22] Filed: Sep. 2, 1981

[30] Foreign Application Priority Data

Sep. 2, 1980 [JP] Japan ............................ 55-121540

[51] Int. Cl.³ ............................................ C07D 498/16
[52] U.S. Cl. ................................. 260/243.3; 544/73; 544/101
[58] Field of Search ............... 544/73, 101; 260/243.3

[56] References Cited

U.S. PATENT DOCUMENTS 3,883,522  5/1975  Gerster ............................. 544/101
3,984,548  10/1976  Gerster ........................... 424/248.53

Primary Examiner—Richard Raymond
Attorney, Agent, or Firm—Sughrue, Mion, Zinn, Macpeak and Seas

[57] ABSTRACT

Pyrido[1,2,3-de][1,4]benzoxazine derivatives are described having the formula (I)

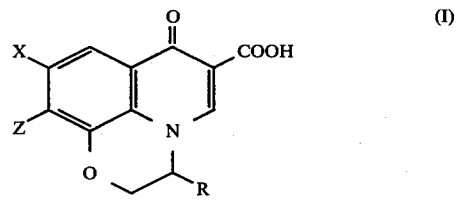

wherein X is a halogen atom, R is a hydrogen atom or an alkyl group of 1 to 6 carbon atoms and Z represents mono-substituted, di-substituted or cyclic-substituted amino group which may contain a hetero atom and may have a substituent such as hydroxyl, alkyl having 1 to 6 carbon atoms, amino, hydroxyalkyl having 1 to 6 carbon atoms or mono- or di-alkylamino having 1 to 6 carbon atoms in each alkyl moiety and the pharmaceutically acceptable salt thereof, having antibacterial activity.

8 Claims, No Drawings

BENZOXAZINE DERIVATIVES

BACKGROUND OF THE INVENTION

U.S. Pat. Nos. 3,883,522 and 3,984,548 describe 9-fluoro-3-methyl-7-oxo-2,3-dihydro-7H-pyrido[1,2,3-de][1,4]benzoxazine-6-carboxylic acid, Japanese Patent application (OPI) No. 138582/1979 describes 1-ethyl-6-fluoro-4-oxo-1,4-dihydro-7-(4-methyl-1-piperazinyl)-quinoline-3-carboxylic acid, and Japanese Patent Application (OPI) No. 76875/1980 describes 8-(4-methyl-1-piperazinyl)-9-fluoro-5-methyl-6,7-dihydro-1-oxo-1H,5H-benz[ij]quinolidine-2-carboxylic acid (the term "OPI" as used herein refers to a "published unexamined patent application").

SUMMARY OF THE INVENTION

This invention relates to a novel anti-bacterial agent, and, more particularly, to 9-halo-7-oxo-2,3-dihydro-7H-pyrido[1,2,3-de][1,4]benzoxazine-6-carboxylic acid derivatives having the formula (I)

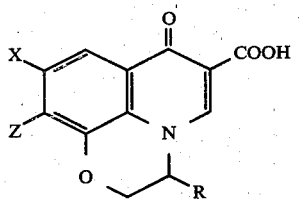

wherein X represents a halogen atom, R represents a hydrogen atom or an alkyl group having from 1 to 6 carbon atoms and Z represents a mono-substituted amino group, a di-substituted amino group, or a cyclic-substituted amino group which may contain another hetero-atom, and the substituted amino group may be further substituted with one or more substituents selected from the group consisting of hydroxyl, alkyl having from 1 to 6 carbon atoms, amino, hydroxyalkyl having from 1 to 6 carbon atoms, monoalkylamino and dialkylamino having from 1 to 6 carbon atoms in each alkyl moiety, and pharmaceutically acceptable salts thereof. Examples of the mono-substituted amino group include monoethylamino or monomethylamino, and examples of the di-substituted amino group include diethylamino or dimethylamino. The expression "cyclic-substituted amino group" refers to a 4- to 7-membered ring and examples thereof include azetidinyl, pyrrolidinyl, piperidinyl, morpholinyl, piperazinyl and homopiperazinyl (hexahydro-1H-1,4-diazepin-1-yl). More particularly, the substituent Z means, for example, 4-methyl-1-piperazinyl, 1-piperazinyl, 1-pyrrolidinyl, 3-hydroxy-1-pyrrolidinyl, 1-piperidinyl, 4-hydroxy-1-piperidinyl, 3-hydroxy-1-piperidinyl, 4-morpholinyl, 4-(2-hydroxyethyl)piperazinyl, 3,5-dimethyl-1-piperazinyl, 4-dimethylamino-1-piperidinyl, homopiperazinyl, 1-pyrazolidinyl, 2-methyl-1-pyrazolidinyl, N-(2-hydroxyethyl)amino, N-(2-hydroxyethyl)-N-methylamino, hydrazyl, and methylhydrazyl.

The compound of this invention can form an acid addition salt with an inorganic or organic acid such as hydrochloric acid, sulfuric acid, methanesulfonic acid and the like and can form the corresponding carboxylate with sodium, potassium and the like. In comparison with the above-described known compounds, the compounds of this invention have more excellent antibacterial activity against gram-negative and gram-positive bacteria, as well as lower toxicity.

DETAILED DESCRIPTION OF THE INVENTION

Compounds according to this invention can be prepared by the reaction illustrated below.

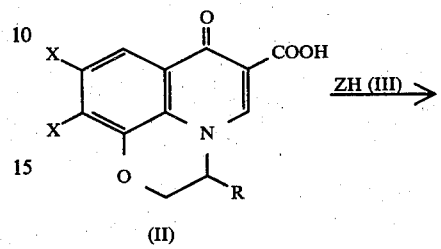

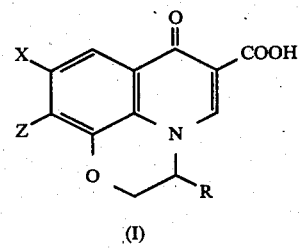

wherein X, R and Z are the same as described above. The reaction may be performed by heating a compound of the formula (II) with an amine of the formula (III) at a temperature of from about 30° C. to 200° C., and preferably from 70° C. to 150° C., in the presence of a suitable organic polar solvent such as dimethylsulfoxide, sulfolane, dimethylformamide, dimethylacetamide or water. It is desirable to carry out the reaction in the presence of an acid-acceptor such as triethylamine, dimethylaniline, potassium carbonate and the like at a molar ratio of 1.0 to 1.2 mol of the acid-acceptor per mol of the compound of the formula (II). As the raw material of the formula (III) is an amine itself, it may act also as the acid-acceptor. In such a case, it is desirable to use two or more moles of the amine of the formula (III) to one mole of the compound of the formula (II). When another acid-acceptor like triethylamine is employed, it may be adequate to use the amine of the formula (III) at a molar ratio of 1.0 to 1.2 mol per mol of the compound of the formula (II).

The reaction is normally completed in a period of from 1 to 48 hours and the product can be isolated and purified by conventional techniques such as evaporation, filtration, extraction, chromatography, recrystallization and a combination thereof. For example, when the product is precipitated by cooling the reaction mixture, it is collected by filtration and if precipitation is not found, the reaction mixture is concentrated to dryness under reduced pressure and the residue is shaken with a mixture of chloroform and water, then the product is obtained by concentrating the chloroform layer. In case the product is colored or contains some by-products, further purification can be performed by a silica gel chromatography or recrystallization.

Starting compounds of the formula (II) of the process for preparing the compound of this invention are novel compounds and can be prepared from known compound (A) [J. Amer. Chem. Soc., 81, 94–101 (1959)] by the method outlined below.

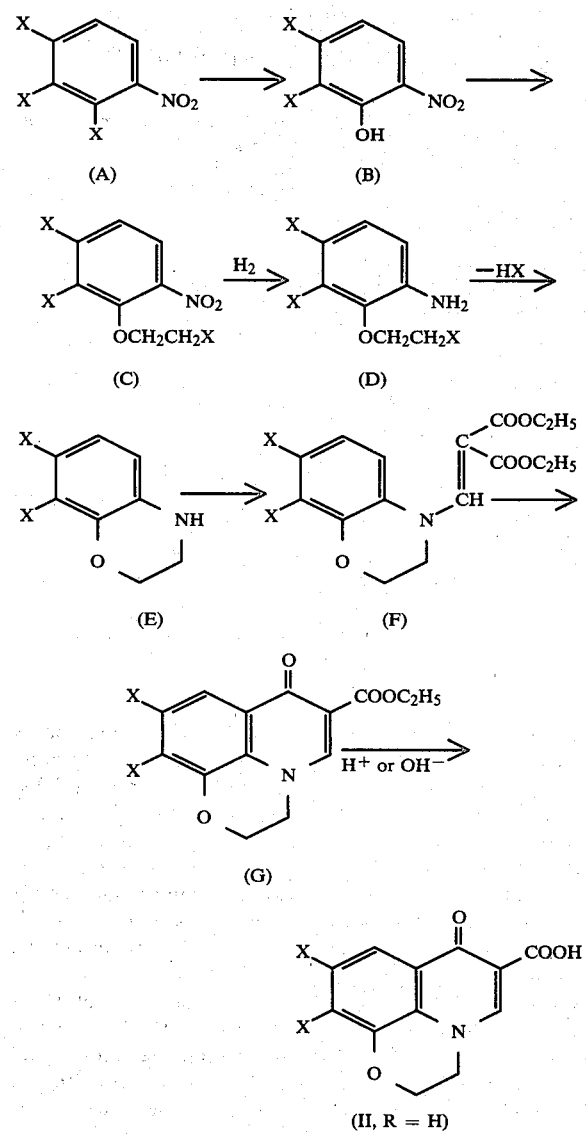

(II, R = H)

In the formula, X represents a halogen atom.

When 2,3,4-trihalonitrobenzene (A) is hydrolyzed in the presence of potassium hydroxide, triethylamine and the like, 2,3-dihalo-6-nitrophenol (B) is produced. The compound (B) is heated with 1,2-dihalogenoethane at a temperature of from about 50° C. to about 150° C., and preferably at from 80° C. to 120° C., while stirring in an organic polar solvent such as ethanol, dimethylformamide or dimethylsulfoxide in the presence of an acid-acceptor such as, inorganic base, for instance potassium carbonate and sodium carbonate, or an organic base, for instance, triethylamine and N,N-dimethylaniline, to produce the compound of the formula (C). The nitro group of the compound (C) is then reduced by a common reduction using sodium dithionite or iron-hydrochloric acid or a catalytical reduction with Raney nickel, and the compound of the formula (D) is produced. When the compound (D) is heated at a temperature of from about 50° C. to 150° C. in the presence of an acid-acceptor which is used in the process (B) to (C), in a polar solvent such as ethanol or dimethylformamide, a benzoxazine derivative (E) is obtained. The benzoxazine derivative (E) is heated with diethyl ethoxymethylenemalonate at from about 80° C. to 150° C. in the presence of a solvent such as ethanol or in the absence of solvent to produce the compound (F). When ring closure reaction is performed by heating the compound (F) at a temperature of from about 120° C. to 150° C. in polyphosphoric acid or an ester thereof, a tricyclic compound (G) is prepared. The ester moiety of the compound (G) is hydrolyzed by a conventional method using an acid or base, the starting compound of the formula (II) wherein substituent R is a hydrogen is obtained. The compounds (B) to (G) are also novel compounds.

In the case wherein substituent R in formula (II) is alkyl, the starting material of the formula (II) can be prepared by a somewhat different process. That is, the compound of the formula (B) described above is heated with a halomethylalkylketone, such as monochloroacetone, at from 50° C. to 150° C. in the presence of an acid-acceptor such as potassium carbonate or sodium carbonate in a polar solvent such as acetone, alcohols or dimethylformamide, preferably in the presence of a catalytic amount of potassium iodide, to produce the compound of the formula (H).

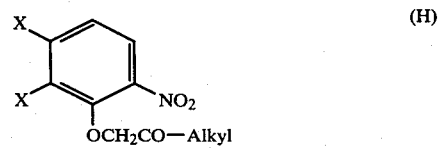

When the compound (H) is catalytically treated with Raney nickel or palladium carbon, reduction of the nitro group, ring closure with dehydration from the resulting amino group and the oxo group and hydrogenation of the resulting double bond proceed simultaneously and a compound of the formula (J) is obtained.

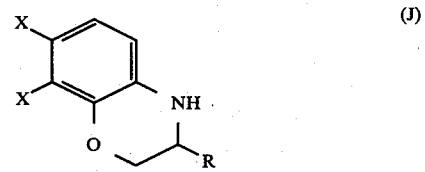

The compound (J) can be converted into the starting material of the formula (II) wherein the substituent R is alkyl according to the method as in the case wherein R is hydrogen.

The antibacterial activity (in vitro) of compounds of this invention (9-fluoro-10-(4-methyl-1-piperazinyl)-3-methyl-7-oxo-2,3-dihydro-7H-pyrido[1,2,3-de][1,4]benzoxazine-6-carboxylic acid (Ia), 9-fluoro-3-methyl-7-oxo-10-(1-piperazinyl)-2,3-dihydro-7H-pyrido[1,2,3-de][1,4]benzoxazine-6-carboxyliac acid (Ib), 9-fluoro-10-(3-hydroxy-1-pyrrolidinyl)-3-methyl-7-oxo-2,3-dihydro-7H-pyrido[1,2,3-de][1,4]benzoxazine-6-carboxylic acid (Ic), and 9-chloro-3-methyl-10-(4-methyl-1-piperazinyl)-7-oxo-2,3-dihydro-7H-pyrido[1,2,3-de][1,4]benzoxazine-6-carboxylic acid (Id) are shown in the following Tables 1 and 2 in comparison with pipemidic acid (8-ethyl-5,8-dihydro-5-oxo-2-(1-piperazinyl)-pyrido[2,3-d]pyrimidine-6-carboxylic acid, a known antibacterial drug)(abbreviated as PPA in Table 1).

TABLE 1

| Test Organisms | Minimum Inhibitory Concentration (MIC, μg/ml)* | | | |
|---|---|---|---|---|
| | PPA | Ia | Ib | Ic |
| Escherichia coli NIHJ | 1.56 | ≦0.025 | ≦0.025 | 0.05 |
| Shigella flexneri 2a, 5503 | 1.56 | 0.05 | 0.05 | 0.1 |
| Proteus vulgaris, 3167 | 1.56 | 0.05 | 0.05 | 0.1 |
| Proteus mirabilis, 1287 | 6.25 | 0.1 | 0.1 | 0.1 |
| Klebsiella pneumoniae, 501 | 6.25 | 0.2 | 0.39 | 0.78 |
| Enterobacter cloacae, 12001 | 1.56 | 0.1 | 0.2 | 0.2 |
| Serratia marcescens, 13001 | 6.25 | 0.2 | 0.78 | 0.78 |
| Pseudomonas aeruginosa, 2063 | 25 | 1.56 | 0.78 | 1.56 |
| Pseudomonas sepacia, II D 1340 | 100 | Not tested | 12.5 | Not tested |
| Staphylococcus aureus, 209 P | 12.5 | 0.39 | 0.39 | 0.1 |
| Streptococcus pyogenes, G-36 | >100 | 1.56 | 3.13 | 0.78 |
| Bacillus subtilis, ATCC 6633 | 6.25 | 0.2 | 0.39 | 0.05 |

*Determined by the standard method of the Japan Society of Chemotherapy: dilution method on plate culture (heart infusion agar culture), $10^6$/ml of bacteria were seeded and incubated at 37° C. for 18 hours.

TABLE 2

| Test Organisms | Minimum Inhibitory Concentration (MIC, μg/ml)* | |
|---|---|---|
| | Ia | Id |
| Escherichia coli NIHJ | ≦0.05 | ≦0.05 |
| Shigella flexneri 2a, 5503 | ≦0.05 | ≦0.05 |
| Proteus vulgaris, 3167 | ≦0.05 | ≦0.05 |
| Proteus mirabilis, 1287 | 0.1 | 0.1 |
| Klebsiella pneumoniae, 501 | 0.39 | 0.2 |
| Enterobacter cloacae, 12001 | 0.1 | ≦0.05 |
| Serratia marcescens, 13001 | 0.1 | 0.1 |
| Pseudomonas aeruginosa, 2063 | 0.78 | 0.78 |
| Pseudomonas sepacia, II D 5132 | 12.5 | 6.25 |
| Staphylococcus aureus, 209 P | 0.39 | 0.2 |
| Streptococcus pyogenes, G-36 | 1.56 | 12.5 |
| Bacillus subtilis, ATCC 6633 | 0.1 | 0.1 |

*Determined in Muller-Hinton Bouillon, $10^6$/ml of bacteria were seeded and incubated at 37° C. for 18 hours.

As can be seen from Tables 1 and 2, the compound of this invention exerts higher antibacterial effect on the test organisms than the known drug. Additionally, the compounds of this invention exhibit very low toxicity. For example, the acute toxicity (LD$_{50}$) of the compound (Ia) is 380 mg/kg, in mice (i.v.).

On the other hand, known compounds, such as 8-(4-methyl-1-piperazinyl)-9-fluoro-5-methyl-6,7-dihydro-1-oxo-1H,5H-benz[ij]quinolizine-2-carboxylic acid (Japanese Patent Application (OPI) No. 76875/1980) and 1-ethyl-6-fluoro-4-oxo-7-(4-methyl-1-piperazinyl)quinoline-3-carboxylic acid (Japanese Patent Application (OPI) No. 138582/1979) have comparatively high toxicity [135 mg/kg and 225 mg/kg, respectively, in mice (i.v.)]. Although PPA has a low toxicity [LD$_{50}$=610 to 649 mg/kg in mice (i.v.)], the anti-bacterial activity of PPA is much weaker than the compounds of this invention as shown in Table above.

The present invention is further illustrated by the following Examples. Unless otherwise indicated, all parts, percents, ratios, and the like are by weight.

EXAMPLE 1

Production of starting material 20 g of 2,3,4-trifluoronitrobenzene was dissolved in 150 ml of dimethyl sulfoxide, and to this mixture a solution of 10% potassium hydroxide was added dropwise while keeping the temperature at 18° to 20° C. Then, the mixture was stirred for 2 hours at room temperature and one liter of water was added to this reaction mixture and the mixture was shaken with chloroform. The water layer was acidified with hydrochloric acid and was extracted with chloroform. The extract was washed with water and was dried, then chloroform layer was concentrated. The residue was purified by silica gel column chromatography to provide 5.8 g of 2,3-difluoro-6-nitrophenol as yellow oil.

7.9 g of the 2,3-difluoro-6-nitrophenol, 50.1 g of 1,2-dibromoethane and 18.7 g of potassium carbonate were added to 80 ml of dimethylformamide and the mixture was stirred for 2.5 hours at from about 80° to 100° C. (bath temperature). The reaction mixture was concentrated to dryness in vacuo and the residue was distributed between ethyl acetate and water. The organic solvent layer was washed with water and was dried, then the solvent was evaporated. The residue was dissolved in benzene and was purified by silica gel column chromatography to provide 7.7 g of 2-(2-bromoethoxy)-3,4-difluoronitrobenzene as light yellow oil.

NMR(CDCl$_3$): δ(ppm)

3.75 (2H, t, J=7 Hz, —CH$_2$Br)

4.62 (2H, t, J=7 Hz, —OCH$_2$—)

6.92–7.04 and 7.65–7.93

(respectively 1H, m, C$^5$-H and C$^6$-H)

1.74 g of this product was dissolved in 30 ml of methanol and a solution of 6.44 g of sodium dithionite dissolved in 15 ml of water was added thereto. The mixture was stirred for 1 hour at room temperature. Methanol was evaporated and the residue was extracted with chloroform. After the extract was washed with water and dried, the solvent was evaporated to provide 0.44 g of 2-(2-bromoethoxy)-3,4-difluoroaniline.

NMR(CDCl$_3$): δ(ppm)

3.67 (2H, t, J=6 Hz, —CH$_2$Br)

3.90 (2H, s, NH$_2$)

4.42 (2H, t, J=6 Hz, —OCH$_2$—)

6.30–6.90 (2H, m, C$^5$-H and C$^6$-H)

1.82 g of this product and 3.03 g of potassium carbonate were added to 10 ml of dimethylformamide and the mixture was stirred for 1 hour at from about 80° to 100° C. (bath temperature). The reaction mixture was added to ice-cold water and was extracted with ethyl acetate. After the extract was washed with water and dried, the solvent was distilled off at room temperature to provide 1.21 g of 7,8-difluoro-2,3-dihydro-4H-[1,4]benzoxazine with m.p. 48°–54° C.

NMR(CDCl$_3$): δ(ppm)

3.38 (2H, t, J=5.5 Hz, —NHCH$_2$—)

3.70 (1H, b.s., NH)

4.28 (2H, t, J=5.5 Hz, —OCH$_2$—)

6.17–6.80 (2H, m, C$^5$-H, C$^6$-H)

The mixture of 1.1 g of this product and 1.38 g of diethyl ethoxymethylenemalonate was stirred for 2 hours at from about 130° to 135° C. (bath temperature). The ethanol produced was evaporated and 20 g of ethyl polyphosphate was added to the residue. Then the mixture was stirred for 1.5 hours at from about 140° to 145° C. (bath temperature). The reaction mixture was added to ice-cold water and was extracted with chloroform. The extract was washed fully with water. After drying, the solvent was evaporated and the residue was recrystallized from ethyl acetate. 1.3 g of ethyl 9,10-difluoro-7-oxo-2,3-dihydro-7H-pyrido[1,2,3-de][1,4]benzoxazine-6-carboxylate was obtained as colorless needles with m.p. 265°–266° C.

NMR(CF$_3$COOH): δ(ppm)

1.58 (3H, t, J=7.5 Hz, —CH$_2$CH$_3$)

4.76 (2H, q, J=7.5 Hz, —CH$_2$CH$_3$)

4.96 (4H, b.s., —CH$_2$—CH$_2$—)

8.17 (1H, q, C$^8$-H)

9.35 (1H, s, C$^5$-H)

1.15 g of this product was added to 12 ml of mixture of concentrated hydrochloric acid and acetic acid (1:4 by volume) and the mixture was stirred for 4 hours at 100° to 110° C. (bath temperature). After cooling, the precipitated crystals were collected by filtration, washed with water, methanol and chloroform to give 0.78 g of 9,10-difluoro-7-oxo-2,3-dihydro-7H-pyrido[1,2,3-de][1,4]-benzoxazine-6-carboxylic acid as colorless needles with m.p. above 300° C.

Analysis for $C_{12}H_7FNO_4$: Calculated: C 53.94, H 2.64, N 5.24: Found: C 53.81, H 2.75, N 5.26.

NMR($CF_3COOH$): δ(ppm)
5.0 (4H, b.s., —$CH_2CH_2$—)
8.17 (1H, q, $C^8$-H)
9.45 (1H, s, $C^5$-H)

EXAMPLE 2

Production of starting material 5.8 g of 2,3-difluoro-6-nitrophenol, 5.0 g of monochloroacetone, 8.0 g of potassium carbonate and 0.8 g of potassium iodide were added to 100 ml of acetone and the mixture was refluxed for 4 hours. After the removal of insoluble material by filtration, the solvent was evaporated and the residue was distributed between chloroform and water. The chloroform layer was washed with water and was dried, then the solvent was evaporated. The residue was treated with n-hexane to provide 5.0 g of 2-acetonyloxy-3,4-difluoronitrobenzene as light yellow crystals with m.p. 61° C.

7.1 g of this product was dissolved in 200 ml of ethanol and 14 ml of Raney-nickel was added to this mixture. The mixture was catalytically reduced under normal atmospheric pressure. After the removal of catalyst by filtration and the evaporation of the solvent, the residue was dissolved in chloroform and decolored by passing through a silica gel column to provide 5.1 g of 7,8-difluoro-2,3-dihydro-3-methyl-4H-benzoxazine in the form of light yellow oil.

The mixture of 4.8 g of this product and 5.3 g of diethyl ethoxymethylenemalonate was heated for 1 hour at from about 140° to 145° C. (bath temperature). After reaction, the ethanol produced was removed by evaporation to provide an oily product. 35 g of ethyl polyphosphate was added thereto and the mixture was stirred for 1 hour at from about 140° to 145° C. (bath temperature). After cooling, the reaction mixture was added to ice-cold water. Precipitate was extracted with 200 ml of chloroform, this procedure was carried out three times, and the extracts were combined and was washed with a 5% potassium hydroxide solution and water. The chloroform layer was dried with sodium sulfate to provide 5.1 g of ethyl 9,10-difluoro-3-methyl-7-oxo-2,3-dihydro-7H-pyrido[1,2,3-de][1,4]benzoxazine-6-carboxylate as white powder with m.p. 261° C.

4.0 g of this product was dissolved in 50 ml of a mixture of concentrated hydrochloric acid and acetic acid (1:4 by volume) and this mixture was refluxed for 3 hours on an oil bath. After cooling the precipitated crystal was collected by filtration, washed thoroughly with water. The crystal was washed with a mixture of ethanol and ether (¼ volume ratio) and was dried in vacuo to provide 3.7 g of 9,10-difluoro-3-methyl-7-oxo-2,3-dihydro-7H-pyrido[1,2,3-de][1,4]benzoxazine-6-carboxylic acid as transparent plates with m.p. above 300° C.

EXAMPLE 3

1.0 g of 9,10-difluoro-3-methyl-7-oxo-2,3-dihydro-7H-pyrido[1,2,3-de][1,4]benzoxazine-6-carboxylic acid and 2.85 g of N-methylpiperazine were added to 15 ml of dimethylsulfoxide. The mixture was stirred at a temperature of from about 100° to 110° C. (bath temperature) for 12 hours and the reaction mixture was concentrated to dryness in vacuo and 40 ml of water was added to the residue. Then the product was extracted with chloroform. The extract was dried and concentrated to dryness in vacuo. The residue was recrystallized from ethanol to provide 550 mg of 9-fluoro-3-methyl-10-(4-methyl-1-piperazinyl)-7-oxo-2,3-dihydro-7H-pyrido[1,2,3-de][1,4]benzoxazine-6-carboxylic acid as colorless needles with m.p. 250°-257° C. (with decomposition).

Analysis for $C_{18}H_{20}FN_3O_4$; Calculated: C 59.82, H 5.58, N 11.63; Found: C 59.62, H 5.59, N 11.65.

EXAMPLE 4

140 mg of 9,10-difluoro-3-methyl-7-oxo-2,3-dihydro-7H-pyrido[1,2,3-de][1,4]benzoxazine-6-carboxylic acid and 404 mg of 4-hydroxypiperidine were added to 2 ml of dimethylsulfoxide. The mixture was stirred at a temperature of from about 100° to 110° C. (bath temperature) for 5.5 hours and the reaction mixture was concentrated to dryness in vacuo. Water was added to the residue and the mixture was neutralized with diluted hydrochloric acid to yield precipitate. The precipitate was collected by filtration, washed with water, and then recrystallized from ethanol to provide 66 mg of 9-fluoro-10-(4-hydroxy-1-piperidinyl)-3-methyl-7-oxo-2,3-dihydro-7H-pyrido[1,2,3-de][1,4]benzoxazine-6-carboxylic acid with m.p. 220°-240° C. (with decomposition).

Analysis for $C_{18}H_{19}FN_2O_5$; Calculated: C 59.66, H 5.29, N 7.73; Found: C 59.24, H 5.26, N 7.65.

EXAMPLE 5

843 mg of 9,10-difluoro-3-methyl-7-oxo-2,3-dihydro-7H-pyrrido[1,2,3-de][1,4]benzoxazine-6-carboxylic acid and 646 mg of 3-hydroxypyrrolidine were added to 10 ml of dimethylsulfoxide. The mixture was stirred at a temperature of from about 100° to 110° C. (bath temperature) for 1 hour and the reaction mixture was concentrated to dryness in vacuo. Water was added to the residue and the insoluble substance was collected by filtration. The substance was recrystallized from a mixture of chloroform and ethanol to provide 450 mg of 9-fluoro-10-(3-hydroxy-1-pyrrolidinyl)-3-methyl-7-oxo-2,3-dihydro-7H-pyrido[1,2,3-de][1,4]benzoxazine-6-carboxylic acid with m.p. 278°-280° C. (with decomposition).

Analysis for $C_{17}H_{17}FN_2O_5$; Calculated: C 58.61, H 4.92, N 8.04; Found: C 58.45, H 5.10, N 7.94.

EXAMPLE 6

In the same manner as in Example 3, 9-fluoro-10-(1-homopiperazinyl)-3-methyl-7-oxo-2,3-dihydro-7H-pyrido[1,2,3-de][1,4]benzozaxazine-6-carboxylic acid with m.p. 230°-234° C. (with decomposition) was produced. This product was dissolved in diluted hydrochloric acid and the solution was concentrated in vacuo. To the residue, ethanol was added. Crystals precipitated were collected by filtration and washed with ethanol to provide 9-fluoro-10-(1-homopiperazinyl)-3-methyl-7-oxo-2,3-dihydro-7H- pyrido[1,2,3-de][1,4]benzoxazine-6-carboxylic acid hydrochloride with m.p. 285°–290° C. (with decomposition).

Analysis for $C_{18}H_{20}FN_3O_4 \cdot HCl \cdot H_2O$; Calculated: C 51.99, H 5.57, N 10.10; Found: C 51.61, H 5.25, N 10.10.

EXAMPLE 7

133 mg of 9,10-difluoro-7-oxo-2,3-dihydro-7H-pyrido[1,2,3-de][1,4]benzoxazine-6-carboxylic acid and 0.2 ml of methylhydrazine were added to 3 ml of dimethylformamide. The mixture was stirred at a temperature of from about 100° to 110° C. (bath temperature) for 7 hours. The reaction mixture was concentrated to dryness in vacuo and the residue was treated with water. The insoluble substance was collected by filtration and recrystallized from ethanol to provide 30 mg of 9-fluoro-10-(1-methylhydrazyl)-7-oxo-2,3-dihydro-7H-pyrido[1,2,3-de][1,4]benzoxazine-6-carboxylic acid as yellow prisms with m.p. 239°–242° C.

Analysis for $C_{13}H_{12}FN_3O_4$; Calculated: C 53.24, H 4.13, N 14.33; Found: C 53.89, H 4.22, N 14.22.

EXAMPLE 8

Production of starting material 10.5 g (0.05 mol) of 2,4-dichloro-3-fluoronitrobenzene was dissolved in 30 ml of dimethyl sulfoxide, and 8 ml of a 10% aqueous solution of sodium hydroxide was added to the mixture, followed by stirring the mixture at a temperature of 60° to 70° C. for 20 hours. After completion of the reaction, 200 ml of water was added thereto and the unreacted starting material was removed by extraction with diethyl ether. The aqueous layer was made acidic with acetic acid and extracted with diethyl ether. The ether extract was dried over sodium sulfate and the ether was distilled off. The resulting residue was purified by silica gel (100 g) column chromatography using chloroform as an eluant to provide 3,4 g (35.5% yield) of 3-chloro-2-fluoro-6-nitrophenol with m.p. 73° C.

A mixture of 3 g (15.7 mmols) of 3-chloro-2-fluoro-6-nitrophenol, 3 ml of chloroacetone and 300 mg of potassium iodide in 50 ml of acetone was refluxed for 6 hours while vigorously stirring. After cooling, any insoluble substance was removed by filtration, and the filtrate was concentrated and purified by silica gel (20 g) column chromatography using chloroform as an eluant to provide 2.5 g (54.5% yield) of 2-acetonyloxy-4-chloro-3-fluoronitrobenzene as an oil.

2.3 g (7.9 mmols) of 2-acetonyloxy-4-chloro-3-fluoronitrobenzene was dissolved in 30 ml of ethanol and catalytically reduced in the presence of 2 g of Raney nickel. After completion of the reduction, the catalyst was removed by filtration, and the filtrate was concentrated. The resulting residue was purified by silica gel (20 g) column chromatography using chloroform as an eluant to provide 1.2 g (75.5% yield) of 7-chloro-8-fluoro-3-methyl-2,3-dihydro-4H-1,4-benzoxazine as an oil.

A mixture of 1.11 g (5.5 mmols) of 7-chloro-8-fluoro-3-methyl-2,3-dihydro-4H-1,4-benzoxazine and 1.4 g (6.2 mmols) of diethyl ethoxymethylenemalonate was stirred for 2 hours while heating at 130°–140° C. (bath temperature). After confirming disappearance of the starting benzoxazine compound by thin-layer chromatography, 5 g of ethyl polyphosphate was added to the reaction mixture and the mixture was again allowed to react for 1 hour at 140° C. (bath temperature). After cooling, 20 ml of water was added to the mixture and the precipitate formed was extracted with 150 ml of chloroform. The chloroform extract was dried with sodium sulfate and chloroform was then distilled off. The resulting residue was purified by silica gel (20 g) column chromatography using methanol-chloroform (5:95 by volume) as an eluant to provide 1.2 g (67.0% yield) of ethyl 9-chloro-10-fluoro-3-methyl-7-oxo-2,3-dihydro-7H-pyrido[1,2,3-de][1,4]benzoxazine-6-carboxylate with m.p. 263°–264° C.

Analysis for $C_{15}H_{13}ClFNO_4$; Calculated: C 55.31, H 4.02, N 4.30; Found: C 55.19, H 3.97, N 4.41.

600 mg (1.8 mmol) of the benzoxazine compound obtained above was dissolved in 5 ml of concentrated hydrochloric acid-acetic acid (1:4 by volume) and the solution was heated at 120° C. (bath temperature) for 6 hours. After cooling, 20 ml of water was added to the reaction solution and the precipitated crystals were collected by filtration, washed thoroughly with water, ethanol-diethyl ether (4:1 by volume) and then diethyl ether, and dried to provide 459 mg (92.4% yield) of 9-chloro-10-fluoro-3-methyl-7-oxo-2,3-dihydro-7H-pyrido[1,2,3-de][1,4]benzoxazine-6-carboxylic acid with m.p. >300° C. as transparent plates.

Analysis for $C_{13}H_9ClFNO_4$; Calculated: C 52.45, H 3.05, N 4.71; Found: C 52.20, H 3.13, N 4.74.

EXAMPLE 9

150 mg (0.5 mmol) of 9-chloro-10-fluoro-3-methyl-7-oxo-2,3-dihydro-7H-pyrido[1,2,3-de][1,4]benzoxazine-6-carboxylic acid was suspended in 3 ml of dimethyl sulfoxide and 150 mg of N-methylpiperazine was added to the suspension. The mixture was then allowed to react at 120°–130° C. (bath temperature) for 6 hours. After cooling, the solvent was distilled off under reduced pressure and the residue was washed with diethyl ether to remove any insoluble substance. The resulting residue was purified by silica gel (7 g) column chromatography using methanol-chloroform (5:95 by volume) and then methanol-chloroform (10:90 by volume) as eluants, and the resulting product was recrystallized from ethanol to provide 65 mg (34.4% yield) of 9-chloro-3-methyl-10-(4-methyl-1-piperazinyl)-7-oxo-2,3-dihydro-7H-pyrido[1,2,3-de][1,4]benzoxazine-6-carboxylic acid as pale yellow fine needles with m.p. 275°–276° C. (with decomposition).

Analysis for $C_{18}H_{20}ClN_3O_4$; Calculated: C 57.22, H 5.34, N 11.12; Found: C 57.20, H, 5.11, N 11.23.

EXAMPLES 10–32

Using the procedures analogous to that described in Example 3 or 4 above, the following products were obtained, which were crystallized from ethanol unless otherwise described:

10. 9-fluoro-10-(4-methyl-1-piperazinyl)-7-oxo-2,3-dihydro-7H-pyrido[1,2,3de][1,4]benzoxazine-6-carboxylic acid as light yellow needles with m.p. 260°–270° C. (dec.)
11. 9-fluoro-10-(N-2-hydroxyethyl-N-methylamino)-7-oxo-2,3-dihydro-7H-pyrido[1,2,3-de][1,4]benzoxazine-6-carboxylic acid as light yellow needles with m.p. 262°–265° C.
12. 9-fluoro-10-(3-hydroxy-1-piperazinyl)-7-oxo-2,3-dihydro-7H-pyrido[1,2,3-de][1,4]benzoxaxine-6-carboxylic acid (crystallized from methanol) as yellow needles with m.p. 270°–277° C. (dec.)
13. 9-fluoro-10-(3-hydroxy-1-piperidinyl)-3-methyl-7-oxo-2,3-dihydro-7H-pyrido[1,2,3-de][1,4]benzoxazine-6-carboxylic acid as light yellow needles with m.p. 267°–273° C. (dec.).

14. 9-fluoro-7-oxo-10-(1-piperazinyl)-2,3-dihydro-7H-pyrido-[1,2,3-de][1,4]benzoxazine-6-carboxylic acid as light yellow needles with m.p. 258°–268° C. (dec.) (crystallized from water).

15. 9-fluoro-3-methyl-10-(4-morpholinyl)-7-oxo-2,3-dihydro-7H-pyrido[1,2,3-de][1,4]benzoxazine-6-carboxylic acid as colorless needles with m.p. >300.

16. 9-fluoro-3-methyl-7-oxo-10-(1-piperazinyl)-2,3-dihydro-7H-pyrido[1,2,3-de][1,4]benzoxazine-6-carboxylic acid as light yellowish white crystals with m.p. 260° C. (dec.).

17. 9-fluoro-10-(4-(2-hydroxyethyl)piperazinyl)-3-methyl-7-oxo-2,3-dihydro-7H-pyrido[1,2,3-de][1,4]benzoxazine-6-carboxylic acid with m.p. 282°–285° C. (dec.).

18. 9-fluoro-3-methyl-10-(1-piperidinyl)-7-oxo-2,3-dihydro-7H-pyrido[1,2,3-de][1,4]benzoxazine-6-carboxylic acid with m.p. 268°–275° C. (dec.).

19. 10-(4-ethyl-1-piperazinyl)-9-fluoro-3-methyl-7-oxo-2,3-dihydro-7H-pyrido[1,2,3-de][1,4]benzoxazine-6-carboxylic acid with m.p. 263.5°–264.5° C.

20. 9-fluoro-3-methyl-7-oxo-10-(1-pyrrolidinyl)-2,3-dihydro-7H-pyrido[1,2,3-de][1,4]benzoxazine-6-carboxylic acid with m.p. 268°–269° C.

21. 10-(4-dimethylamino-1-piperidinyl)-9-fluoro-3-methyl-7-oxo-2,3-dihydro-7H-pyrido[1,2,3-de][1,4-]benzoxazine-6-carboxylic acid with m.p. 245°–248° C. (dec.).

22. 10-dimethylamino-9-fluoro-3-methyl-7-oxo-2,3-dihydro-7H-pyrido[1,2,3-de][1,4]benzoxazine-6-carboxylic acid with m.p. 233°–235° C.

23. 9-fluoro-3-methyl-10-(4-methyl-1-homopiperazinyl)-7-oxo-2,3-dihydro-7H-pyrido[1,2,3-de][1,4]benzoxazine-6-carboxylic acid with m.p. 234°–237° C. (dec.).

24. 9-fluoro-3-methyl-10-(2-methyl-1-pyrazolidinyl)-7-oxo-2,3-dihydro-7H-pyrido[1,2,3-de][1,4]benzoxazine-6-carboxylic acid with m.p. 233°–236° C.

25. 9-fluoro-3-methyl-7-oxo-10-(1-pyrazolidinyl)-2,3-dihydro-7H-pyrido[1,2,3-de][1,4]benzoxazine-6-carboxylic acid with m.p. 215°–225° C. (dec.).

26. 9-fluoro-10-(3-hydroxy-1-azetidinyl)-3-methyl-7-oxo-2,3-dihydro-7H-pyrido[1,2,3-de][1,4]benzoxazine-6-carboxylic acid with m.p. 286°–286.5° C. (crystallized from chloroform-ethanol).

27. 9-fluoro-3-methyl-7-oxo-10-(4-thiamorpholinyl)-2,3-dihydro-7H-pyrido[1,2,3-de][1,4]benzoxazine-6-carboxylic acid with m.p. >300° C. (crystallized from chloroform-ethanol).

28. 9-fluoro-10-(3-hydroxymethyl-1-pyrrolidinyl)-3-methyl-7-oxo-2,3-dihydro-7H-pyrido[1,2,3-de][1,4-]benzoxazine-6-carboxylic acid with m.p. 237° C. (crystallized from chloroform-ethanol).

29. 9-fluoro-10-(2-hydroxymethyl-1-pyrrolidinyl)-3-methyl-7-oxo-2,3-dihydro-7H-pyrido[1,2,3-de][1,4-]benzoxazine-6-carboxylic acid with m.p. 265° C. (crystallized from chloroform-ethanol).

30. 9-fluoro-10-(4-hydroxymethyl-1-piperidinyl)-3-methyl-7-oxo-2,3-dihydro-7H-pyrido[1,2,3-de][1,4-]benzoxazine-6-carboxylic acid with m.p. 266° C.

31. 9-fluoro-10-(3-hydroxymethyl-1-piperidinyl)-3-methyl-7-oxo-2,3-dihydro-7H-pyrido[1,2,3-de][1,4-]benzoxazine-6-carboxylic acid with m.p. 222° C.

32. 10-(4-amino-1-piperidinyl)-9-fluoro-3-methyl-7-oxo-2,3-dihydro-7H-pyrido[1,2,3-de][1,4]benzoxazine-6-carboxylic acid (after reacting the compound (II) with 4 tert-butoxycarbonyl aminopiperidine, the protected product was treated with trifluoroacetic acid to remove tert-butoxy carbonyl group. The final product contains crystal water (3/2 $H_2O$) and melts at 150°–151° C. with elevating temperature, then is crystallized at 170°–180° C. and melts again at 210°–212° C.).

REFERENCE EXAMPLE

The compounds of this invention are effective antibacterial agents for treatment of various infectious diseases such as urinary tract infections or infections in respiratory organs in mammals including human. These compounds are used normally by oral administration but they can be administered also by injection or can be used by external application depending upon the type of diseases to be treated.

For the oral administration, the compounds can be used at a dosage between about 100 mg to about 1000 mg in adult human per day, normally at 100 mg to 600 mg, in the form of various pharmaceutical preparations such as tablets, capsules, powder, granule, syrup and the like which are well known in the art. Other preparations suitable for injection or external application can also be prepared by the technique known in the art. For example, pharmaceutical preparations can be prepared by a method known per se using suitable diluents, bindings, disintegrators, coating agents and the like.

An example of the preparation containing the compound (Ia) suitable for oral administration is described below.

| Capsules | |
|---|---|
| Compound (Ia) | 100.0 mg |
| Corn Starch | 23.0 mg |
| CMC Calcium | 22.5 mg |
| Hydroxypropylmethyl Cellulose | 3.0 mg |
| Magnesium Stearate | 1.5 mg |
| Total | 150.0 mg per one capsule |

While the invention has been described in detail and with reference to specific embodiments thereof, it will be apparent to one skilled in the art that various changes and modifications can be made therein without departing from the spirit and scope thereof.

What we claim is:

1. A compound having the formula (I)

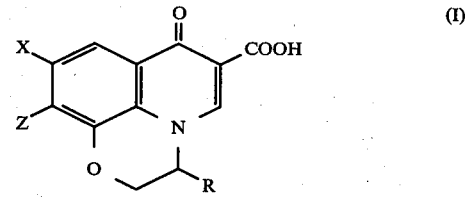

wherein X is a halogen atom, R is a hydrogen atom or an alkyl group having from 1 to 6 carbon atoms and Z represents (1) a mono-alkylamino or di-alkylamino group or (2) a cyclicamino group selected from the group consisting of azetidinyl, pyrrolidinyl, piperdinyl, morpholinyl, piperidinyl, homopiperazinyl, thiamorpholinyl and pyrazolidinyl, each of which amino groups may be substituted with a hydroxyl group, an alkyl group having 1 to 6 carbon atoms, an amino group, a hydroxyalkyl group having 1 to 6 carbon atoms or a mono- or di-alkylamino group having 1 to 6 carbon atoms in each alkyl group.

2. A compound having the formula (I)

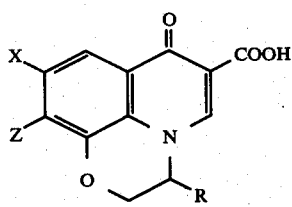

wherein X is a halogen atom, R is a hydrogen atom or an alkyl group having from 1 to 6 carbon atoms and Z represents (1) a mono-alkylamino or di-alkylamino group having 1 to 6 carbon atoms in each alkyl group which may be substituted with a hydroxyl group or an amino (-NH$_2$) group, or (2) a cyclicamino group selected from the group consisting of azetidinyl, pyrrolidinyl, piperidinyl, morpholinyl, piperazinyl, homopiperazinyl, thiamorpholinyl and pyrazolidinyl, each of which cyclic-amino group may be substituted with a hydroxyl group, an alkyl group having 1 to 6 carbon atoms, an amino group, a hydroxyalkyl group having 1 to 6 carbon atoms or a di-alkylamino group having 1 to 6 carbon atoms in each alkyl group.

3. A compound as in claim 1, wherein Z represents a mono-substituted amino group selected from monoethylamino and monomethylamino, a di-substituted amino group selected from diethylamino and dimethylamino, and a cyclic-substituted amino group comprising a 4- to 7-membered ring selected from azetidinyl, pyrrolidinyl, piperidinyl, morpholinyl, piperazinyl and homopiperazinyl.

4. A compound as in claim 1, wherein R is methyl and Z is 4-methyl-1-piperazinyl.

5. A compound as in claim 1, wherein R is methyl and Z is 4-hydroxy-1-piperazinyl.

6. A compound as in claim 1, wherein R is methyl and Z is 3-hydroxy-1-pyrrolidinyl.

7. A compound as in claim 1, wherein R is methyl and Z is homopiperazinyl.

8. The compound 9-fluoro-3-methyl-10-(4-methyl-1-piperazinyl)-7-oxo-2,3-dihydro-7H-pyrido[1,2,3-de][1,4]benzoxazine-6-carboxylic acid.

* * * * *

UNITED STATES PATENT AND TRADEMARK OFFICE

CERTIFICATE EXTENDING PATENT TERM
UNDER 35 U.S.C. 156

Patent No.     : 4,382,892

Dated          : May 10, 1983

Inventor(s)    : Isao Hayakawa et al

Patent Owner   : Daiichi Seiyaku Co., Ltd.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 U.S.C. 156 (b).

I have caused the seal of the Patent and Trademark Office to be affixed this 30th day of December, 1991.

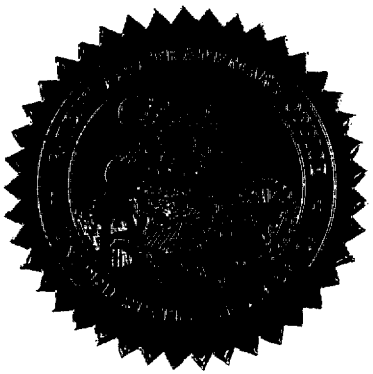

Harry F. Manbeck, Jr.
Assistant Secretary and Commissioner
  of Patents and Trademarks

UNITED STATES PATENT AND TRADEMARK OFFICE
CERTIFICATE OF CORRECTION

PATENT NO. : 4,382,892

DATED : May 10, 1983

INVENTOR(S) : HAYAKAWA, ET AL.

It is certified that error appears in the above-identified patent and that said Letters Patent is hereby corrected as shown below:

In column 12, line 63, delete "piperdinyl" and insert -- piperidinyl --.

In column 12, line 64, delete "piperidinyl" and insert -- piperazinyl --.

Signed and Sealed this

Twelfth Day of May, 1992

Attest:

DOUGLAS B. COMER

*Attesting Officer*     *Acting Commissioner of Patents and Trademarks*